United States Patent
Pinkhasik et al.

(10) Patent No.: US 6,537,209 B1
(45) Date of Patent: Mar. 25, 2003

(54) OPTICAL SYSTEM OF LATERAL OBSERVATION ENDOSCOPE

(75) Inventors: Naum Pinkhasik, San Ramon, CA (US); Lev E. Sorin, St. Petersburg (RU)

(73) Assignee: Itconcepts, Inc., Dublin, CA (US)

( * ) Notice: Subject to any disclaimer, the term of this patent is extended or adjusted under 35 U.S.C. 154(b) by 103 days.

(21) Appl. No.: 09/661,207

(22) Filed: Sep. 14, 2000

(51) Int. Cl.[7] ............................. A61B 1/00; G01N 21/01
(52) U.S. Cl. ...................... 600/170; 600/173; 600/175; 600/176; 356/241.5
(58) Field of Search ................................. 600/170, 171, 600/173, 175, 176; 356/241.1, 241.3, 241.5; 359/367, 831, 833, 834; 385/119; 433/29, 30

(56) References Cited

U.S. PATENT DOCUMENTS

| | | | |
|---|---|---|---|
| 3,481,660 A | | 12/1969 | Sheldon |
| 3,520,587 A | | 7/1970 | Tasaki et al. |
| 3,548,808 A | * | 12/1970 | Takahashi et al. ........... 385/118 |
| 3,619,030 A | * | 11/1971 | Tomii et al. .............. 250/227.2 |
| 4,195,904 A | * | 4/1980 | Yamashita ................... 359/367 |
| 4,281,929 A | * | 8/1981 | Lord et al. ................ 356/241.1 |
| 4,387,969 A | * | 6/1983 | Nishioka et al. ............ 359/726 |
| 4,678,290 A | | 7/1987 | Welker |
| 4,727,859 A | | 3/1988 | Lia |
| 4,941,457 A | * | 7/1990 | Hasegawa ................. 356/241.4 |
| 5,700,236 A | * | 12/1997 | Sauer et al. ................. 600/121 |

FOREIGN PATENT DOCUMENTS

| | | |
|---|---|---|
| DE | N 3716401 | 11/1987 |
| JP | N 4-4567 | 1/1992 |

* cited by examiner

*Primary Examiner*—John P. Leubecker
(74) *Attorney, Agent, or Firm*—Dorsey & Whitney LLP

(57) ABSTRACT

An optical system of an endoscope for investigation and observation of spaces in medicine and engineering. The construction permits the panoramic observation of the internal surface of the space or channel. The endoscope contains a tube in which a lens is installed along the axis of symmetry and coaxial along the entire internal surface of the tube a longitudinal fiber illumination light guide is installed. A lateral observation nozzle is installed on the tube with the possibility of unlimited rotation around the tube. The nozzle is provided with a unit of two reflection prisms, one is meant for lateral observation and the other for lateral illumination. The lateral observation prism is incorporated into the body of the lateral illumination prism. A diaphragm overlapping the face of the lateral observation prism presented to the lens is arranged, on the nozzle. A visor from the opaque sheet material overlaps a part of the longitudinal fiber light guide which projects beyond the overall dimensions of the prism unit.

11 Claims, 3 Drawing Sheets

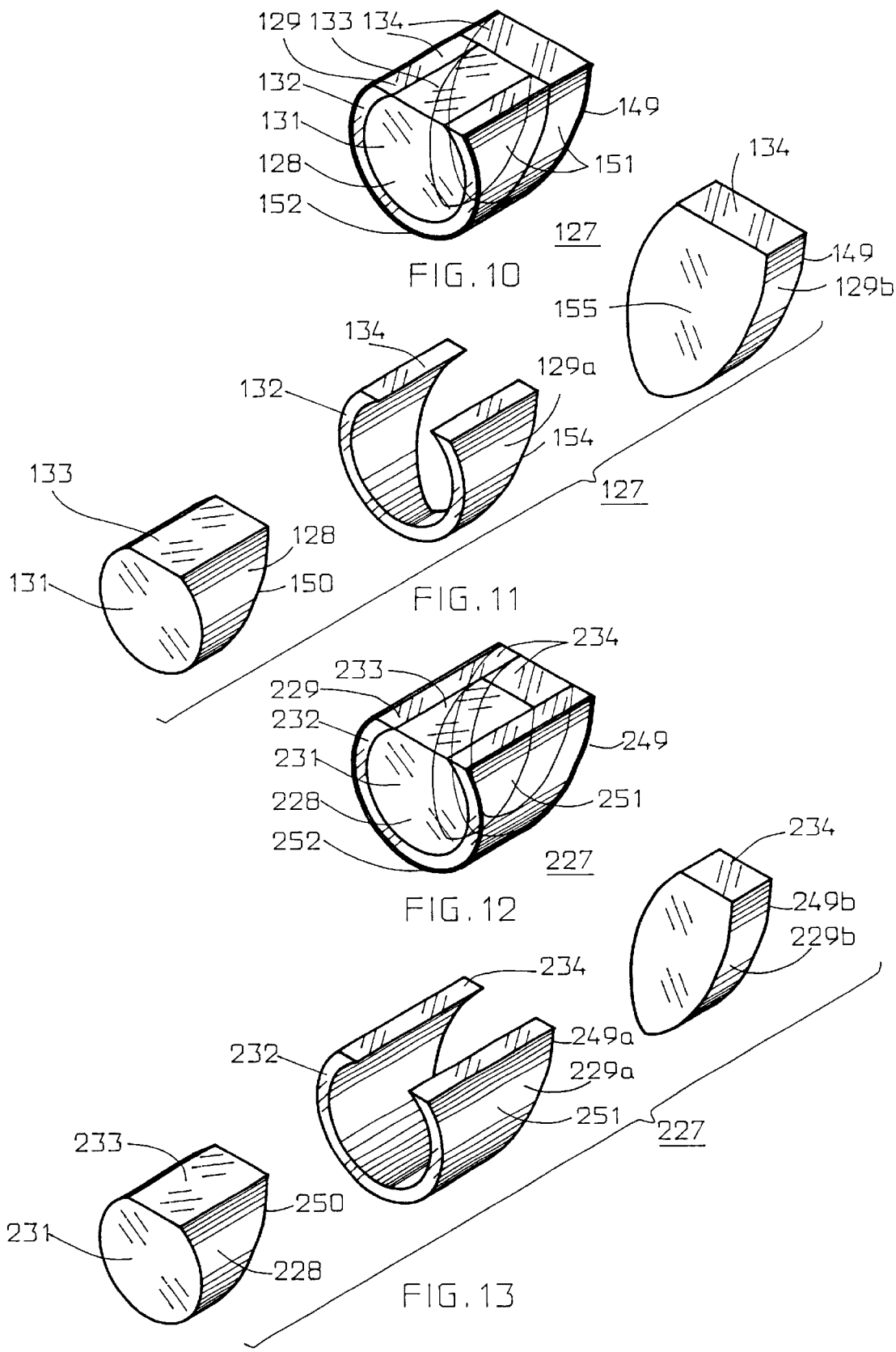

OPTICAL SYSTEM OF LATERAL OBSERVATION ENDOSCOPE

FIELD OF THE INVENTION

This invention relates to devices and instruments for medical examination of cavities and to devices for observation of internal surfaces of hollow bodies and tubes and more particularly to constructions of optical systems for examination and observation of spaces in medicine and engineering, particularly with respect to endoscopes. Such optical systems are used when it is necessary to transmit an internal space image for visual examination, photographing, displaying on a monitor screen.

BACKGROUND OF THE INVENTION

Constructions of optical systems for observation of spaces are known in medicine and engineering. Most often optical systems contain a tube housing where observation system and illumination channel light guides are arranged. The construction elements for observation or registration are placed on one end of the flexible or rigid tube housing, the other end is introduced into a space and contains elements for image transformation and illumination elements. The observed part of the internal surface is illuminated with the help of the illumination channel and the optical observation system allows investigation of the internal space surface. Quite often it is necessary to investigate lateral space surfaces. In this case the elements allowing a change in the direction of optical observation into lateral in respect to the optical system axis are introduced.

The following inventions can serve as examples of such constructions.

In the invention according to the DE application N 3716401, Int.Cl. A 61 B 1/00 entitled "Endoscope nozzle" and published on Nov. 19, 1987, the nozzle is fixed with the help of a joint on an endoscope housing. It contains a lens with an element for observation direction changing relative to an optical axis of the lens and a light guide of an illumination channel. The optical axes of the observation channel and the illumination channel do not coincide with each other. That's why the nozzle is fixed to the endoscope rigidly and one has to rotate the entire endoscope housing for observation of different surface points.

The Japanese application N 4-4567 entitled "Rigid endoscope of inclined vision" contains a mount, an optical system for observation and a light guide. The mount and the light guide are placed in a tube housing. The optical axes of the observation and illumination system for lateral direction are deflected at an angle with respect to the lens optical axis with the help of a prism. In order to observe the entire lateral surface along the whole transverse perimeter of the investigated cavity it is also necessary to rotate the entire endoscope housing around the axis of symmetry.

"Fiber optic inspection device" according to U.S. Pat. No. 3,481,660 issued on Dec. 2, 1969 contains a lens in a mount and illumination lamps installed in a housing in a lateral wall of which a window is provided. The lateral observation is performed due to a reflection prism situated opposite the window. For panoramic observation of the walls in a space it is necessary to rotate the entire housing of the fiber optic inspection device. "Stereoscopic endoscope" according to U.S. Pat. No. 3,520,587 issued on Jul. 14, 1970 contains a stereoscopic optical system for lateral observation and a lateral illumination channel fixed in the tube-shaped housing not in line. Each observation system contains a lens and a reflection prism placed opposite a window provided in a housing wall. The illumination system contains a light guide and the reflection prism. Both systems are rigidly fixed in the endoscope housing. For observation of the entire surface in the space with the help of the observation system, it is necessary to rotate the entire endoscope housing around the axis.

"Apparatus for visual inspection of closed machinery" according to U.S. Pat. No. 4,678,290 issued on Jul. 7, 1987 contains a tube-shaped housing with a lateral window, a lateral observation optical system and a lateral illumination system. The housing is filled with inert gas which provides safety from explosion of the apparatus during usage. Both systems of observation and illumination are fixedly attached in the housing of the inspection apparatus to perform panoramic observation through rotating the entire endoscope housing connected by wires with the auxiliary equipment.

U.S. Pat. No. 4,727,859 issued on Mar. 1, 1988 "Right angle detachable prism assembly for borescope" discloses a device for investigation of the internal spaces contains a tube where an image transmission channel and an illumination channel are situated not in line with the tube. A head containing two closely arranged prisms installed in a common mount is connected to the tube. One prism is used for illumination of the lateral surface of the investigated space and the second prism is used for image transmission in case of lateral viewing.

In order to observe the entire surface of the space or channel using this device it is necessary to rotate the tube together with the head around the longitudinal axis which is not always convenient because the device is connected by wires with the auxiliary equipment.

The object of the declared invention is to create an optical system of lateral observation endoscope to perform panoramic observation of the internal surface of a space or channel due to rotation of only the lateral observation nozzle around the optical axis of the endoscope by an unlimited angle.

The achievement of the mentioned object will make the endoscope application more convenient and will enlarge its possibilities.

Another object of the invention is to obtain a construction where a beam of lateral illumination and a beam of lateral observation converge spatially which provides better observation conditions.

Another object of the invention is to make an endoscope application more convenient as well as to improve the quality of optical observation of the internal space or tube with the help of the endoscope.

Other objects and advantages of the present invention will be disclosed when considering the detailed description and drawings.

SUMMARY OF THE INVENTION

An optical system of the lateral observation endoscope is provided in the form of a tube where the lens is installed along the axis of symmetry and a longitudinal fiber illumination light guide is arranged along the entire internal surface of the tube.

The lateral observation nozzle is installed on the tube, whose housing is tube-shaped with a window in the lateral wall and is installed on the tube in line with the possibility of unlimited rotation around the tube for panoramic lateral observation.

The lateral observation nozzle is provided with a unit of two reflection prisms, one of which is meant for lateral observation and the other prism for lateral illumination. The lateral observation prism is incorporated into the lateral illumination prism body in such a way that each of two refracting faces of one prism lies in the plane of the matched faces of another prism. In this case, the refracting faces of the lateral- illumination prism cover faces of the lateral observation prism on three sides. In this case the illumination beam illuminates more uniformly the observed surface section which is situated in the view field of the lateral observation prism.

The prism unit is installed in the housing of the nozzle in such a way that one pair of the matched refracting faces of both prisms lies in the plane perpendicular to the optical axis of the lens, in this case the-refracting face of the lateral observation prism is arranged opposite the lens installed along the tube symmetry axis and the matched with the face of the lateral illumination gob prism being arranged opposite the end face of the longitudinal fiber illumination light guide. Another pair of refracting faces adjacent to the mentioned pair, is oriented towards the lateral window provided in the wall of the nozzle housing.

The integration of the lateral observation prism with the lateral illumination prism in the prism unit along the entire surface of their mutual contact is opaque. That's why light from the lateral illumination prism does not penetrate to the lateral observation prism. The diaphragm is arranged on the nozzle from the side facing the mentioned lens, and is in the form of a figure overlapping the face of the lateral observation prism facing the lens and contains a hole in line with the optical axis of the lens. The diaphragm prevents penetration of scattered light from the longitudinal fiber illumination light guide to the lateral observation prism.

There is a visor in the construction of the nozzle which is provided from the opaque sheet material in the form of a circle segment installed on the nozzle from the side of the longitudinal fiber light guide and overlaps that part which projects beyond the overall dimensions of the prism unit from the side of the lateral window provided in the wall of the nozzle housing. The visor prevents the face of the lateral observation prism presented to the lateral window in the wall of the nozzle housing from illumination by the beams coming from the part of the fiber light guide which projects beyond the overall dimensions of the prism unit.

Due to the fact that the lens is installed along the axis of symmetry in the endoscope tube, the longitudinal fiber illumination light guide is situated coaxial along the entire internal surface of the tube and the nozzle provided with the prism unit is installed on the endoscope tube with the possibility of unlimited rotation around the tube, it is possible to perform panoramic observations without resort to rotation of the entire endoscope. It is possible to rotate the nozzle using the clamp provided on the external surface of the nozzle housing.

In the prism unit, the lateral observation prism is incorporated into the body of the lateral illumination prism in such a way that the refracting faces of one prism lie in the planes of the matched faces of another prism, the refracting faces of the lateral illumination prism covering the refracting face of the lateral observation prism on three sides. Due to this fact, the illumination beams illuminate more uniformly the whole section of the observed surface being in the view field of the lateral observation prism.

There is no mixing of optical flows of illumination and observation channels because the integration of the lateral observation prism and the lateral illumination prism in the unit along the entire surface of their mutual contact is opaque.

The reflecting face of the lateral observation prism and the reflecting face of the lateral illumination prism can be provided with a light reflecting coating.

The endoscope application becomes more convenient and the quality of surface image transmission of the investigated space or channel is improved.

The prism unit containing the lateral observation prism and the lateral illumination prism can be provided in different ways.

In a first variant, the main cross-section of the lateral observation prism has the form of a right-angled triangle. The lateral surface of the lateral illumination prism is cylindrical according to the form of the aforementioned tube-shaped nozzle housing and is provided with a light reflecting coating. This variant of the prism unit contains the least number of components.

In a second variant, the lateral observation prism incorporated into the body of the lateral illumination prism is in the form of a round cylindrical body, one end face of which is upright and the other inclined to the axis of symmetry. A longitudinal flat shear provided on the lateral surface of the cylindrical body, in this case the upright end face, and adjacent lateral longitudinal flat shear are the refracting faces of the lateral observation prism. The inclined end face of the cylindrical body is the reflection face of the lateral observation prism.

In this variant, the lateral illumination prism is built-up from the tube element and the end attachment. The one end of the tube element is upright and its plane coincides with the plane of the upright end face of the cylindrical body of the lateral observation prism. The second end face of the tube element is inclined to the axis of symmetry and its plane coincides with the plane of the inclined end face of the cylindrical body of the lateral observation prism. The end attachment is in the form of an inclined cylinder with the diameter equal to the external diameter of the tube element and with both end faces inclined to the same side relative to the axis of symmetry.

The end attachment by its one end face is attached to the inclined end face of the aforementioned tube element by optically transparent adhesive. The, longitudinal flat joint shear is provided in the wall of the tube element and on the lateral surface of the end attachment whose plane coincides with the plane of the longitudinal shear of the mentioned cylindrical body of the lateral observation prism arranged in the tube element. The upright end of the tube element and the adjacent to it longitudinal flat joint shear of the tube element and the end attachment are the refracting faces of the lateral illumination prism. The inclined external end face of the end attachment is the reflection face of the lateral illumination prism. The lateral round cylindrical joint surface of the tube element and the end attachment of the lateral illumination prism is provided with a light reflecting coating.

In a third variant, the lateral observation prism incorporated into the body of the lateral illumination prism is in the form of a round cylindrical body in the same way as in the second variant.

The lateral illumination prism is built-up from the tube element and the end insert.

The internal diameter of the tube element corresponds to the external diameter of the aforementioned cylindrical body of the lateral observation prism. The one end face of the tube element is upright and its plane coincides with the plane of the upright end face of the cylindrical body of the lateral observation prism, the second end face of the tube element is inclined to the axis of symmetry.

Behind the inclined end face of the cylindrical body of the lateral observation prism the cylindrical end insert is installed in the tube element by means of an optically transparent adhesive the diameter of which is equal to the internal diameter of the tube element and the plane of the external end face of the end insert coincides with the plane of the inclined end face of the tube element.

The longitudinal flat joint shear is provided jointly in the wall of the tube element and on the lateral surface of the end insert, its plane coincides with the plane of the longitudinal shear of the cylindrical body of the lateral observation prism arranged in the tube element. The upright end of the tube element and the adjacent lateral longitudinal flat joint shear of the tube element and the end insert are the refracting faces of the lateral illumination prism.

Arranged in the same plane, the mentioned inclined end face of the tube element and the inclined end face of the end insert are the reflecting faces of the lateral illumination prism. The lateral external surface of the tube element of the lateral illumination prism is provided with a light reflecting coating.

The second and the third variants of the prism unit embodiment contain more components but they are more adaptable to streamlined production.

BRIEF DESCRIPTION OF THE DRAWINGS

The invention is illustrated by the following drawings.

FIG. 10 is a prism unit where the lateral illumination prism is executed from the tube element and the end attachment.

FIG. 11 is an assembly diagram of the prism unit according to FIG. 10.

FIG. 12 is a prism unit where the lateral illumination prism is executed from the tube element and the end insert.

FIG. 13 is an assembly diagram of the prism unit according to FIG. 12.

DETAILED DESCRIPTION OF THE PREFERRED EMBODIMENT

The optical system of the lateral observation endoscope in FIGS. 1, 2, 3 and 4 contains a tube 21 in which along the axis of symmetry a lens 22 is installed and coaxial along the entire internal surface of the tube 21 there is a longitudinal fiber illumination light guide 23. A lateral observation nozzle 24 is installed on the tube 21.

Figure 3:
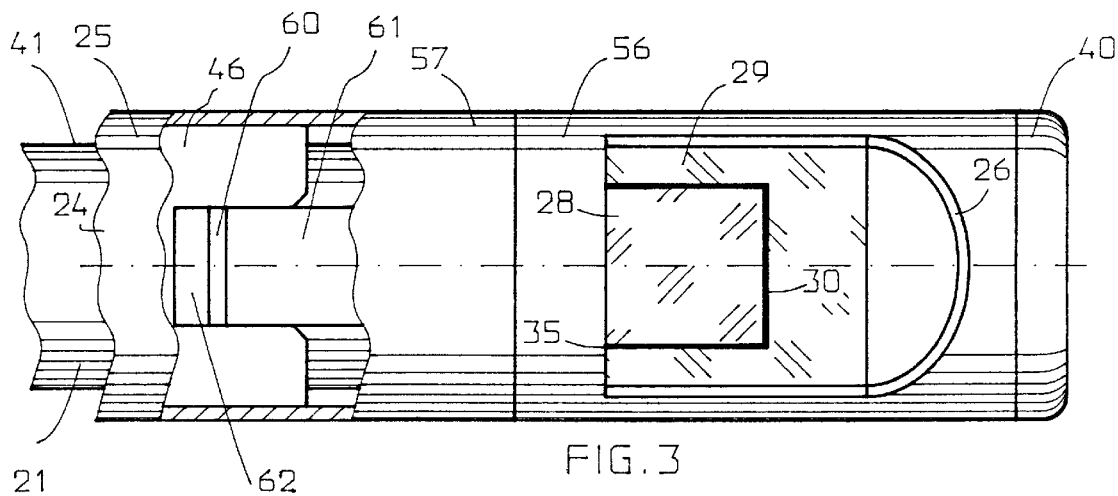
FIG. 3 is a view of the window in the lateral wall of the nozzle housing, 3—3 in FIG. 2.

Near the lateral observation nozzle 24 the housing 25 is tube-shaped with a window 26 in a lateral wall in FIG. 3. The housing 25 is installed in line on the tube 21 with the possibility of unlimited rotation around the tube 21 for panoramic lateral observation.

Figure 1:
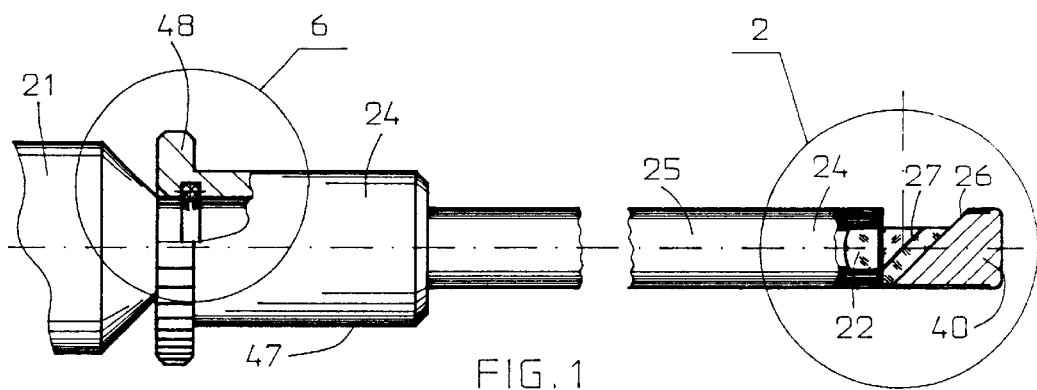
FIG. 1 is a general view of the optical system of the lateral observation endoscope.
Figure 2:
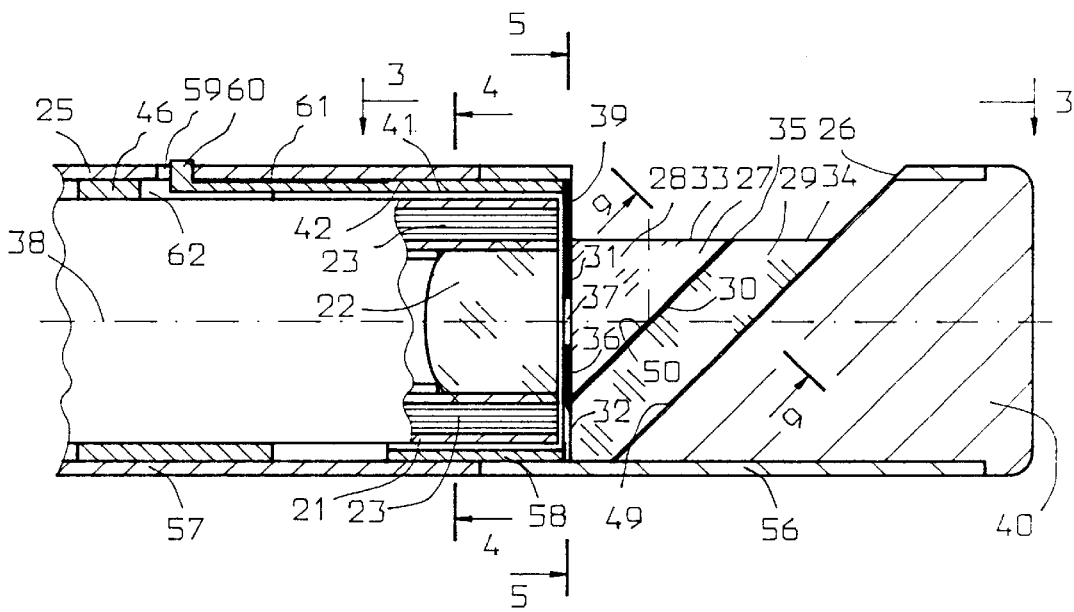
FIG. 2 is a lateral observation nozzle installed on the tube, view 2 in FIG. 1.

The lateral observation nozzle 24 in FIGS. 1, 2 and 3 is provided with a unit 27 of two reflection prisms, one of which, a prism 28, is meant for lateral observation and the second, a prism 29, is meant for lateral illumination. The lateral observation prism 28 is incorporated into the body of the lateral illumination prism 29 in which a corresponding hollow or recess 30 is made in FIGS. 2, 3, 7 and 9.

In FIG. 2 a refracting face 31 of the lateral observation prism 28 and a refracting face 32 of the lateral illumination prism 29 lie in the same plane perpendicular to the optical axis of the lens 22. In this case the refracting face 31 of the lateral observation prism 28 is arranged opposite the lens 22 and the refracting face 32 of the lateral illumination prism 29 is arranged opposite the end face of the longitudinal fiber illumination light guide 23.

The another pair of refracting faces adjacent to the described pair of faces, namely a face 33 of the lateral observation prism 28 and lying in the same plane a face 34 of the lateral illumination prism 29, are oriented towards the lateral window 26 provided in the wall of the housing 25 of the lateral observation nozzle 24.

In the place of mutual contact of the lateral observation prism 28 and the lateral illumination prism 29 at their integration into the unit 27 an opaque interlayer 35, for example from black mastic, is placed in FIGS. 2, 3, 7, 8 and 9.

Figure 5:
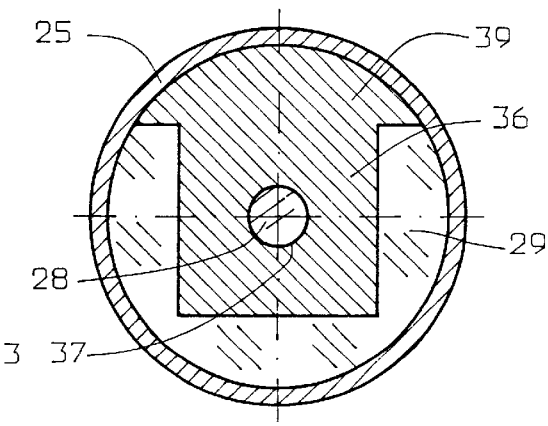
FIG. 5 is a cross-section of the nozzle along 5—5, the allocation place of the diaphragm and the visor in FIG. 2.

In the housing 25 of the lateral observation nozzle 24 FIGS. 2, 5, a diaphragm 36 is installed which is arranged from the side facing the lens 22. The diaphragm 36 is in the form of a flat figure overlapping the face 31 of the lateral observation prism 28 facing the lens 22 and contains a hole 37 in line with an optical axis 38 of the lens 22. The diaphragm 36 can be in the form of an opaque layer deposited on the refracting face 31 of the lateral observation prism 28.

In the housing 25 of the lateral observation nozzle 24 in FIGS. 2, 5, a visor 39 is installed which is provided from the opaque sheet material and has a form of a circle segment. The visor 39 is installed from the side of the longitudinal fiber light guide 23 and overlaps that part which projects beyond the overall dimensions of the prism unit 27 from the side of the lateral window 26 of the housing 25 of the nozzle 24. FIGS. 2 and 5 show a variant where the diaphragm 36 and the visor 39 are provided as a single whole from the opaque sheet material.

In the front end of the tube-shaped housing 25 of the lateral observation nozzle 24, a blank plug 40 is installed in order to prevent ingress of foreign objects in FIGS. 1, 2 and 3.

Figures 6, 7:
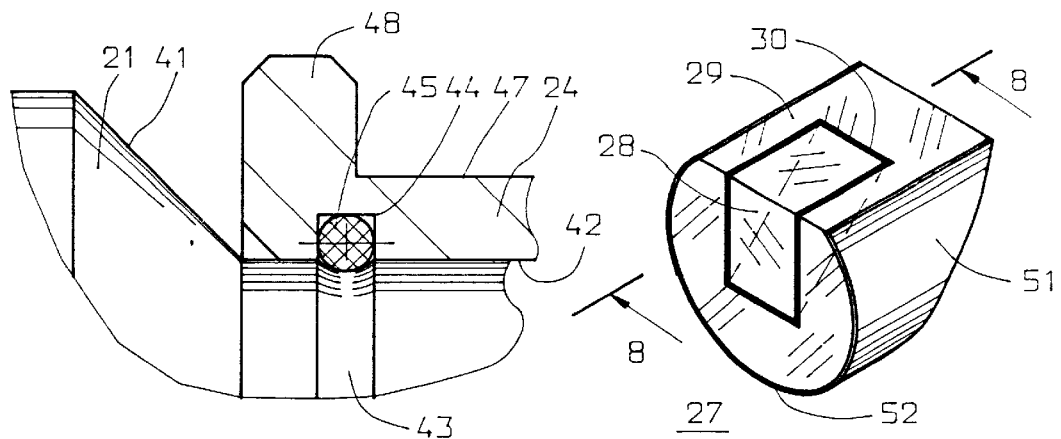
FIG. 6 is a fixing unit of, the lateral observation nozzle on the endoscope tube with the elastic ring, view 6 in FIG. 1.
FIG. 7 is a prism unit with the lateral observation prism having flat inter parallel, lateral faces.

On an external surface 41 of the tube 21 and on an internal surface 42 of the end of the tube-shaped housing 25 of the nozzle 24 on the tube 21 in FIG. 6, oppositely arranged rings of grooves 43 and 44 are provided. In the groove 44 provided on the internal surface 42 of the end of the tube-shaped housing 25 of the nozzle 24, a ring 45 from the elastic material is arranged projecting beyond the mentioned surface 42 and contacting the groove 43 provided on the external surface 41 of the tube 21. The ring 45 prevents spontaneous longitudinal displacement of the nozzle 24 relative to the tube 21.

On the internal surface 42 of the housing 25 of the nozzle 24, a guide bush 46 is installed by means of which the housing 25 of the nozzle 24 bears against the external surface 41 of the tube 21 in FIG. 2.

On an external surface 47 of the housing 25 of the nozzle 24 in FIGS. 1, 6, a clamp 48 is provided which serves for the manual rotation of the lateral observation nozzle 24 around the tube 21 in case of panoramic round observation of the internal surface of the investigated space or channel.

In the prism unit 27 in FIG. 2, a reflecting face 49 of the lateral illumination prism 29 is arranged parallel to a reflecting face 50 of the lateral observation prism 28.

Figure 8:
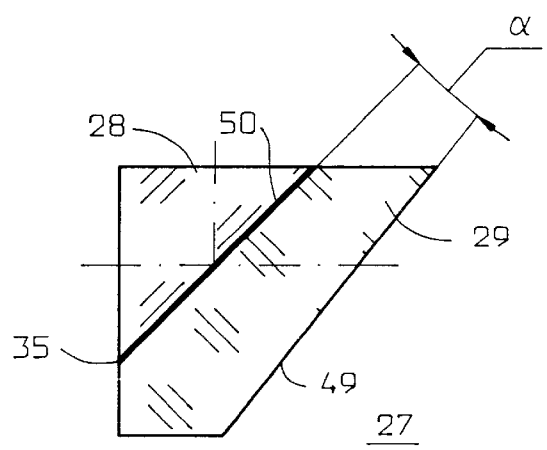
FIG. 8 is a prism unit with the lateral illumination prism which has a reflecting face situated at an angle of α with the reflecting face of the lateral observation prism, cross-section 8—8 in FIG. 7.

For improving the illumination uniformity at a small distance from the endoscope to the observation object, the reflecting face 49 of the lateral illumination prism 29 can be provided at an angle of a equal to 1°–10° with the plane of the reflecting face 50 of the lateral observation prism 28 in the prism unit 27 in FIG. 8.

The lateral surface 51 of the lateral illumination prism 29 in FIG. 7 is round and cylindrical according to the form of the tube-shaped housing 25 of the lateral observation nozzle 24 and is provided with a light reflecting coating 52.

Figure 9:
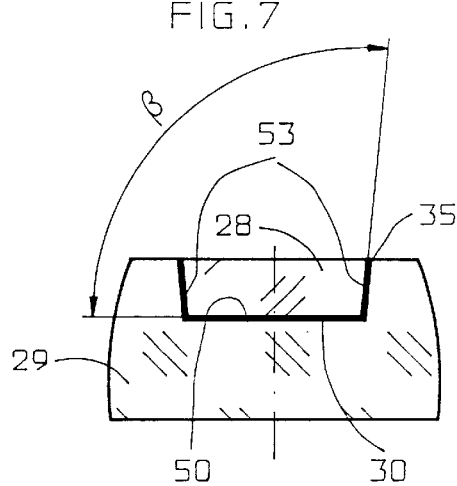
FIG. 9 is an installation example of the lateral observation prism in the lateral illumination prism, cross-section 9—9 in FIG. 2.

In order to simplify the installation procedure of the lateral observation prism 28 into the hollow 30 provided in the lateral illumination prism 29, the lateral observation prism 28 is provided with a base 53 arranged at an angle of α equal to 95°–100° with the plane of its reflecting face 50 in FIG. 9 and in the lateral illumination prism 29 the hollow is executed in a congruous form.

FIGS. 10 and 11 show the second embodiment variant of the prism unit 127. The lateral observation prism 128 incorporated into the body of the lateral illumination prism 129 is in the form of a round cylindrical body, its one end face 131 is upright and the other end face 150 is inclined to the axis of symmetry of the cylindrical body.

A longitudinal flat shear 133 is provided on the lateral surface of the cylindrical body. The upright end face 131 and the adjacent to it lateral longitudinal flat shear 133 are the refracting faces of the lateral observation prism 128.

The inclined end face 150 of the cylindrical body of the lateral observation prism 128 is the reflecting face and can be provided with a light reflecting coating.

The lateral illumination prism 129 is built-up from a tube element 129a and an end attachment 129b. The one end face 132 of the tube element 129a is upright and its plane coincides with the plane of the upright end face 131 of the cylindrical body of the lateral observation prism 128.

The second end face 154 of the tube element 129a is inclined to the axis of symmetry and its plane coincides with the plane of the inclined end face 150 of the cylindrical body of the lateral observation prism 128.

The end attachment 129b is in the form of an inclined cylinder with the diameter equal to the external diameter of the tube element 129a and inclined towards the same side relative to the axis of symmetry of both end faces 155 and 149.

The end attachment 129b, by its one end face 155 is attached with an optically transparent adhesive to the inclined end face 154 of the tube element 129a.

In the wall of the tube element 129a and on the lateral surface of the end attachment 129b, the longitudinal flat joint shear 134 is provided, the plane of which coincides with the plane of the longitudinal shear 133 of the cylindrical body of the lateral observation prism 128. The upright end face 132 of the tube element 129a and the adjacent to it lateral longitudinal flat joint shear 134 of the tube element 129a and the end attachment 129b are the refracting faces of the lateral illumination prism 129.

The inclined external end face 149 of the end attachment 129b is the reflecting face of the lateral illumination prism 129 and can be provided with a light reflecting coating. The lateral external round cylindrical joint surface 151 of the tube element 129a and end attachment 129b of the lateral illumination prism 129 is provided with a light reflecting coating 152.

FIGS. 12 and 13 represent a third variant of the prism unit embodiment. The lateral observation prism 228 incorporated into the body of the lateral illumination prism 229 is in the form of a round cylindrical body, its one end face 231 is upright the other end face 250 is inclined to the axis of symmetry of the cylindrical body in the same way as in the second variant of the prism unit 127 described above.

On the lateral surface of the cylindrical body, the longitudinal flat shear 233 is provided. The upright end face 231 and adjacent to it lateral longitudinal flat shear 233 are the refracting faces of the lateral observation prism 228.

The inclined end face 250 of the cylindrical body of the lateral observation prism 228 is the reflecting face and can be provided with a light reflecting coating.

The lateral illumination prism 229 is built-up from the tube element 229a and the end insert 229b.

The internal diameter of the tube element 229a corresponds to the external diameter of the cylindrical body of the lateral observation prism 228 and to the diameter of the end insert 229b.

The one end face 232 of the tube element 229a is upright and its plane coincides with the plane of the upright end face 231 of the cylindrical body of the lateral observation prism 228, the second end face 249a of the tube element 229a is inclined to the axis of symmetry.

Behind the inclined end face 250 of the cylindrical body of the lateral observation prism 228, the cylindrical end insert 229b is installed in the tube element 229a by means of an optically transparent adhesive applied on the mated cylindrical surfaces of the tube element 229a and the end insert 229b. In this case, the plane of the external end face 249b of the end insert 229b coincides with the plane of the inclined end face 249a of the tube element 229a. The end faces 249a and 249b form the joint reflecting face 249 of the lateral illumination prism 229.

In the wall of the tube element 229a and on the lateral surface of the end insert 229b, the longitudinal flat joint shear 234 is provided, the plane of which coincides with the plane of the longitudinal shear 233 of the cylindrical body of the lateral observation prism 228 arranged in the tube element 229a. The upright end face 232 of the tube element 229a and the adjacent to it lateral longitudinal flat joint shear of the tube element 229a and the end insert 229b are the refracting faces of the lateral illumination prism 229.

The inclined end face 249a of the tube element 229a and the inclined end face 249b of the end insert 229b arranged in the same plane form jointly the reflecting face 249 of the lateral illumination prism 229 and can be provided with a light reflecting coating. The lateral round external surface 251 of the tube element 229a, being at the same time the lateral round external surface of the lateral illumination prism 229, is provided with a light reflecting coating 252.

The tube-shaped housing 25 of the lateral observation nozzle 24 is provided from the intersplit head 56 and tail part 57 joined with each other in line by means of a coupling 58. The head 56 is rigidly fixed on the one end of the coupling 58. The tail part 57 is freely fitted over the other end of the coupling 58. In a wall of the tail part 57, a hole 59 is provided wherein a hook 60 of a (stop) catch spring 61 is introduced which is rigidly fastened with the coupling 58 and is tightened to the internal surface 42 of the tail part 57 of the tube-shaped housing 25 due to its elasticity. In this case, a gap between the spring catch 61 and the external surface 41 of the tube 21 is less than the height of the hook 60 of the spring catch 61 so as to exclude spontaneous mutual disconnection of the head 56 and the tail part 57 of the housing 25 under operating conditions. The disconnection of the head 56 and the tail part 57 is possible only after the removal of the tube-shaped housing 25 from the tube 21. After the removal of the tube-shaped housing 25 from the tube 21, it is possible to take the hook 60 out from the hole 59, folding the spring catch 61 inside the tube-shaped housing 25.

The disconnection of the head 56 and the tail part 57 reduces labor when cleaning the refracting face 31 of the lateral observation prism 28 and the refracting face 32 of the lateral illumination prism 29 from possible contamination.

A longitudinal recess 62 arranged opposite the hole 59 provided in the wall of the tail part 57 is provided in the bush 46. The width of the recess 62 is equal to the width of the spring catch, 61. The spring catch 61 is arranged in the recess 62 of the bush 46 and holds the hook 60 in the hole 59 due to its elasticity, which prevents the head 56 and the tail part 57 of the housing 25 of the nozzle 24 from shifting and mutual axis turning.

The optical system of the lateral observation endoscope is used in the following way.

The endoscope, with the lateral observation nozzle 24 installed on the tube 21, is introduced into the investigated space for the observation of its internal surface. The window 26 in the lateral wall of the housing 25 of the lateral observation nozzle 24 is directed to the observed object by the rotation of the lateral observation nozzle 24 around the tube 21. The rotation of the nozzle 24 is performed manually using the clamp 48 provided on the housing 25 of the nozzle 24 which permits ease of endoscope handling and fast panoramic observation of the entire internal surface of the investigated space (FIGS. 1 and 6).

Figure 4:
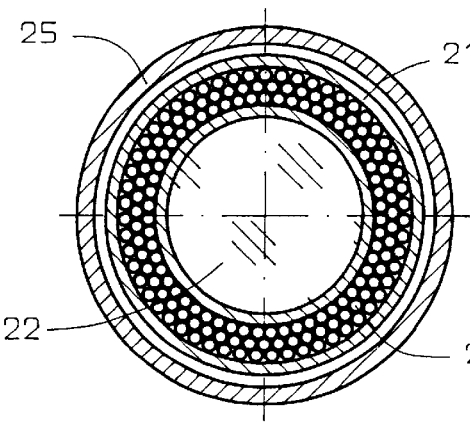
FIG. 4 is a cross-section of the tube with the nozzle along 4—4 in FIG. 2.

The illumination of the observed object is performed by a light flow feed through the longitudinal fiber illumination light guide 23 arranged coaxial along the entire internal surface of the tube 21 (FIGS. 2, 3 and 4). The light flow enters the lateral illumination prism 29 and changes direction due to reflection from the reflecting face 49 of the lateral illumination prism 29 and then comes out through the refracting face 34 for presentation to the window 26 in the lateral wall of the housing 25 of the lateral observation nozzle 24. Light from the fiber light guide 23 enters only the lateral illumination prism 29 at any rotation of the nozzle 24.

The observation of the investigated space surface is carried out through the lens 22 and the lateral observation prism 28. The image is formed with the help of the lens 22. The diaphragm 36 overlaps the face 31 of the lateral observation prism 28 facing lens 22. Due to this fact, light from the fiber illumination light guide 23 does not enter the lateral observation prism 28. The hole 37 provided in the diaphragm 36 lets the image beams pass from the lateral observation prism 28 to the lens 22.

Light from the fiber light guide 23 does not enter the refracting face 33 of the lateral observation prism 28 because the part of the fiber light guide 23 projecting beyond the overall dimensions of the prism unit 27 from the side of the lateral window 26 is overlapped by the visor 39 fixed in the nozzle 24 (FIGS. 2 and 5).

Due to the fact that the lateral observation prism 28 is incorporated into the lateral illumination prism 29 and is covered by the latter on three sides the illumination uniformity of the observed surface of the investigated space is improved and image contrast range is greatly improved too.

The prism unit 27 is provides as a single whole but light from the lateral illumination prism 29 does not penetrate to the lateral observation prism 28 because the integration of prisms 28 and 29 into the unit 27 along the entire surface of their mutual contact is opaque. For this purpose, before the installation of the lateral observation prism 28 into the hollow 30 provided in the lateral illumination prism 29, the entire surface of the hollow 30 is covered with the opaque interlayer 35 from black paint or mastic.

The visor 39 and the diaphragm 36 can be provided as a single whole from the opaque sheet material. They can be provided separately, for example, the diaphragm 36 can be applied on the face 31 of the lateral observation prism 28 in the form of the opaque coating.

Easy rotation of the lateral observation nozzle 24 is provided by the installation of the elastic ring 45 between the tube 21 and the nozzle 24 near one end of the nozzle 24 as well as by the bush 46 installed on the internal surface 42 of the housing 25 of the nozzle 24 (FIGS. 2 and 6).

When cleaning from contamination the refracting face 31 of the lateral observation prism 28 and the refracting face 32 of the lateral illumination prism 29, the tube-shaped housing 25 is first removed from the tube 21. After that, the spring catch 61 is folded by acting on the hook 60 inside the tube-shaped housing 25. The hook 60 is taken out from the hole 59. Then the head 56 and the tail part 57 of the tube-shaped housing 25 of the nozzle 24 are disconnected.

The plug 40 installed in the front end of the tube-shaped housing 25 of the nozzle 24 prevents ingress of foreign objects to the nozzle 24 (FIGS. 1 and 2).

The prism unit 27 can be provided in different variants. The most preferable embodiment variants are given in FIGS. 2, 7, 8, 9, 10 and 12.

In the first variant in FIGS. 2, 7, 8 and 9 the lateral illumination prism 29 is one-piece with the hollow 30 for the lateral observation prism 28. The lateral observation prism 28 can be made with the main cross-section in the form of an isosceles right triangle and installed by means of an opaque interlayer 35 in the, hollow 30 of the lateral illumination prism 29.

The first variant of the prism unit embodiment has the least number of components.

In the second and in the third embodiments of prism units 127 and 227, the lateral observation prism 128 and 228 is provided from the cylindrical body where the refracting faces 131, 133 and 231 and 233 are formed by the upright end face and the longitudinal flat shear and the reflecting face 150 and 250 is formed by the inclined end face of the cylindrical body. Such prisms 128 and 228 are provided from a cylindrical blank.

The lateral illumination prisms 129 and 229 in the second and third variants are built-up from tube and cylindrical blanks.

In the second variant, the lateral illumination prism 129 is provided from the tube element 129a and the end attachment 129b, and in the third variant, from the tube element 229a and the end insert 229*b*. The prisms 129 and 229 are formed by machine processing of tube and cylindrical blanks and the components are cemented together by an optically transparent adhesive. Such creation of the prism is quite adaptable to streamlined production.

In all embodiment variants of the prism unit 27, 127 and 227, the reflecting face 49, 149 and 249 of the lateral illumination prisms 29, 129 and 229 can be arranged either parallel or at an angle of $\alpha$ equal to $1°$–$10°$ with the plane of the reflecting face 50, 150 and 250 of the lateral observation prisms 28, 128 and 228. The arrangement of the reflecting face 49, 149 and 249 at an angle of $\alpha$ improves the illumination uniformity at small distances from the endoscope to the observation object.

In order to avoid losses of the illumination light flow, the lateral cylindrical round surfaces 51, 151 and 251 of the lateral illumination prisms 29, 129 and 229 in each three variants correspondingly are provided with the light reflecting coating 52, 152 and 252.

Due to the proposed construction of the optical system of the lateral observation endoscope, the panoramic observation of the internal surface of the investigated space or channel is carried out by the rotation of the lateral observation nozzle 24 around the endoscope tube 21 through an unlimited angle, which improves convenience of investigation.

Due to the fact that in each prism unit 27, 127 and 227 the corresponding prism 28, 128, and 228 of the lateral observation is incorporated into the body of the corresponding prism 29, 129 and 229 of the lateral illumination the uniformity of illumination, of the observed surface of the investigated space is improved.

What is claimed is:

1. An optical system of a lateral observation endoscope comprising:
   (a) a tube in which a lens is installed along an axis of symmetry and a longitudinal fiber light guide is coaxial along an internal surface of the tube;
   (b) a lateral observation nozzle having a tube-shaped housing with a window in a lateral wall and being installed on the tube for rotation around the tube to permit panoramic lateral observation;
   (c) the lateral observation nozzle being provided with a unit of two reflecting prisms, one of which is meant for lateral observation and the other of which is meant for lateral illumination, the lateral observation prism being incorporated into the lateral illumination prism so that each of two refracting faces of the one prism lies in a plane of a corresponding face of the other prism;
   (d) the prism unit being installed in the nozzle housing so that one pair of the corresponding faces of the prisms lies in a plane perpendicular to the optical axis of the lens, a reflecting face of the lateral observation prism being arranged opposite the lens and the corresponding face of the lateral illumination prism being arranged opposite an end face of the longitudinal fiber illumination light guide, the another pair of corresponding faces of the prisms being oriented towards the window provided in the wall of the nozzle housing;
   (e) the integration of the lateral observation prism and the lateral illumination prism in one unit along the entire surface of their mutual contact being opaque;
   (f) a diaphragm arranged on the nozzle from a side facing the lens and in the form of a figure overlapping the face of the lateral observation prism presented to the lens, the diaphragm containing a hole in line with the optical axis of the lens; and
   (g) a visor provided from an opaque sheet material and having the form of a circle segment installed on the nozzle from a side of the longitudinal fiber light guide and overlapping that part which projects beyond the overall dimensions of the prism unit from the lateral window provided in the wall of the nozzle housing.

2. An optical system of a lateral observation endoscope as defined in claim 1 wherein the reflecting face of the lateral illumination prism is arranged parallel relative to the face of the lateral observation prism.

3. An optical system of a lateral observation endoscope as defined in claim 1 wherein the reflecting face of the lateral illumination prism is arranged at an angle of $\alpha$ equal to $1°$–$10°$ with the plane of the face of the lateral observation prism, a vertex of the dihedral angle $\alpha$ being arranged from a side of the faces of both prisms oriented towards the lateral window provided in the wall of the nozzle housing.

4. An optical system of a lateral observation endoscope as defined in claim 1 wherein a main cross-section of the lateral observation prism has the form of an isosceles right-angled triangle.

5. An optical system of a lateral observation endoscope as defined in claim 1 wherein the lateral observation prism is provided with interparallel bases and a hollow is provided in the lateral illumination prism so that the lateral observation prism is installed flush with the faces of the lateral illumination prism.

6. An optical system of a lateral observation endoscope as defined in claim 1 wherein the lateral observation prism is provided with bases arranged at an angle of $\beta$ equal to $95°$–$100°$ with the plane of the reflecting face of the lateral observation prism, a hollow being provided in the lateral illumination prism in which the lateral observation prism is installed flush with the faces of the lateral illumination prism.

7. An optical system of a lateral observation endoscope as defined in claim 1 wherein the reflecting face of the lateral observation prism and a reflecting face of the lateral illumination prism are each provided with a light reflecting coating.

8. An optical system of a lateral observation endoscope as defined in claim 1 wherein a lateral surface of the lateral illumination prism is cylindrical according to the form of the tube-shaped housing of the lateral observation nozzle and is provided with a light reflecting coating.

9. An optical system of a lateral observation endoscope as defined in claim 1 wherein the diaphragm is in the form of an opaque layer deposited on the face of the lateral observation prism presented to the lens.

10. An optical system of a lateral observation endoscope as defined in claim 1 wherein the diaphragm and the visor are provided jointly from the opaque sheet material.

11. An optical system of a lateral observation endoscope as defined in claim 1 wherein the tube-shaped housing of the lateral observation nozzles is provided from an intersplit head and tail part joined with each other in line by a coupling, the coupling having one end on which the head is fixed and another end on which the tail part is fitted freely, the tail part having a hole into which a hook of a spring catch is introduced, the spring catch being rigidly fastened with the coupling and tightened to an internal surface of the tail part due to its elasticity, a gap between the spring catch and the tube introduced into the tube-shaped housing being less than the height of the spring catch hook.

\* \* \* \* \*